(12) United States Patent
Pall et al.

(10) Patent No.: US 8,524,666 B2
(45) Date of Patent: Sep. 3, 2013

(54) METHODS OF USING VIMENTIN TO INHIBIT ANGIOGENESIS AND ENDOTHELIAL CELL PROLIFERATION

(75) Inventors: Taavi Pall, Tiskre Kula (EE); Wally Anderson, Tallinn (EE); Lagle Kasak, Tallinn (EE); Anne Pink, Tallinn (EE); Priit Kogerman, Tabasalu (EE); Aire Allikas, Tallinn (EE); Andres Valkna, Viimsi (EE)

(73) Assignee: IBCC Holding AS, Tallinn (EE)

( * ) Notice: Subject to any disclaimer, the term of this patent is extended or adjusted under 35 U.S.C. 154(b) by 202 days.

(21) Appl. No.: 13/142,541

(22) PCT Filed: Jul. 4, 2008

(86) PCT No.: PCT/EP2008/058697
§ 371 (c)(1),
(2), (4) Date: Oct. 6, 2011

(87) PCT Pub. No.: WO2009/010409
PCT Pub. Date: Jan. 22, 2009

(65) Prior Publication Data
US 2012/0021974 A1    Jan. 26, 2012

Related U.S. Application Data

(60) Provisional application No. 60/949,518, filed on Jul. 13, 2007.

(51) Int. Cl.
| | | |
|---|---|---|
| *A61K 38/00* | (2006.01) |
| *A61P 35/00* | (2006.01) |
| *A61P 17/00* | (2006.01) |
| *A61P 29/00* | (2006.01) |
| *A61P 35/04* | (2006.01) |
| *C07K 14/515* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 1/00* | (2006.01) |
| *C07K 14/00* | (2006.01) |

(52) U.S. Cl.
USPC ....... 514/13.3; 514/18.7; 514/19.2; 514/19.3; 514/19.8; 530/324; 530/350

(58) Field of Classification Search
None
See application file for complete search history.

(56) References Cited

U.S. PATENT DOCUMENTS

| 7,485,414 B2 * | 2/2009 | Lorens et al. ............... 435/4 |
| 2010/0260667 A1 * | 10/2010 | Georges et al. ............ 424/1.49 |

FOREIGN PATENT DOCUMENTS

| WO | WO2004/030615 | 4/2004 |
| WO | WO2007/039255 | 4/2007 |
| WO | WO2007/072221 | 6/2007 |

* cited by examiner

*Primary Examiner* — Robert Landsman
(74) *Attorney, Agent, or Firm* — Gearhart Law, LLC

(57) ABSTRACT

The invention relates to a method of treatment for states related to inhibition of angiogenesis and endothelial cell proliferation comprising administering an effective amount of vimentin or its derivatives or its fragments, to a subject in need thereof. Further, the invention relates to a pharmaceutical composition and a medicament comprising vimentin, as well as the use of vimentin in the manufacture of a medicament. Hereby, angiogenesis and endothelial cell proliferation can be controlled, and therapeutic treatment for related states is provided.

13 Claims, 14 Drawing Sheets

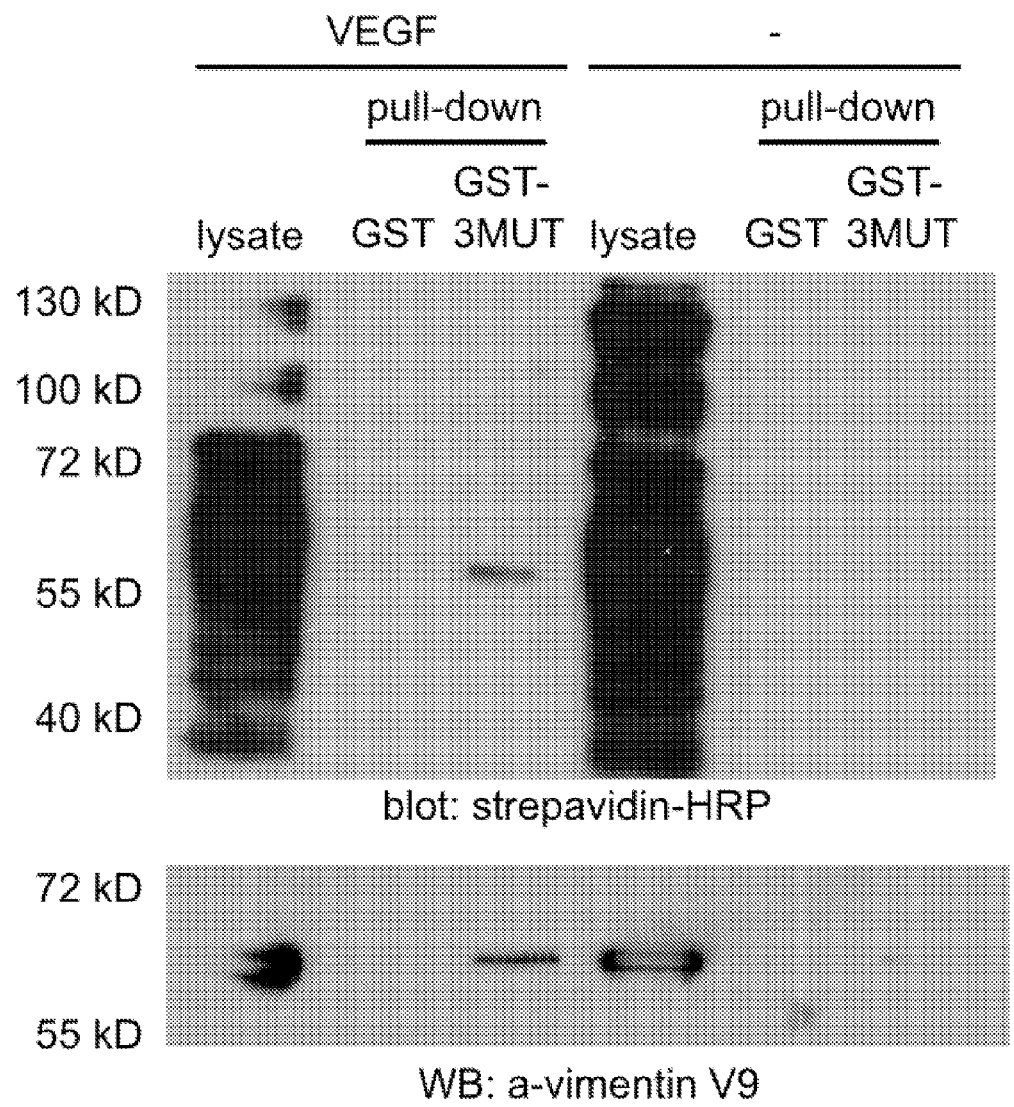
Fig 2b (top) and 2c (bottom).

```
Blast alignment of Mesocricetus auratus (Mesau) vimentin aa sequence to Homo
sapiens (Hsa) vimentin. For Mesau, mismatches to Hsa sequence are shown.

Score  = 867 bits (2239),  Expect = 0.0
Identities = 452/466 (96%), Positives = 461/466 (98%), Gaps = 1/466 (0%)

Hsa      1   MSTRSVSSSSYRRMFGGPGTASRPSSSSRSYVTTSTRTYSLGSALRPSTSRSLYASSPGGV  60
Mesau    1   ....................SN.Q..N.................-............A   59

Hsa     61   YATRSSAVRLRSSVPGVRLLQDSDSVDFSLADAINTEFKNTRTNEKVELQELNDRFANYIDK 120
Mesau   60   .V.......M..................................................119

Hsa    121   VRFLEQQNKILLAELEQLKGQGKSRLGDLYEEEMRELRRQVDQLTNDKARVEVERDNLAE  180
Mesau  120   ............................................................179

Hsa    181   DIMRLREKLQEEMLQREEAENTLQSFRQDVDNASLARLDLERKVESLQEEIAFLKKLHEE  240
Mesau  180   ..........................S.................................D.239

Hsa    241   EIQELQAQIQEQHVQIDVDVSKPDLTAALRDVRQQYESVAAKNLQEAEEWYKSKFADLSE  300
Mesau  240   ............................................................299

Hsa    301   AANRNNDALRQAKQESTEYRRQVQSLTCEVDALKGTNESLERQMREMEENFAVEAANYQD  360
Mesau  300   ................N...........................................L..359

Hsa    361   TIGRLQDEIQNMKEEMARHLREYQDLLNVKMALDIEIATYRKLLEGEESRISLPLPNFSS  420
Mesau  360   ............................................................419

Hsa    421   LNLRETNLDSLPLVDTHSKRTLLIKTVETRDGQVINETSQHHDDLE  466
Mesau  420   ........E.....................................  465
```

Fig 8.

METHODS OF USING VIMENTIN TO INHIBIT ANGIOGENESIS AND ENDOTHELIAL CELL PROLIFERATION

SEQUENCE LISTING

This application contains nucleotide sequence and amino acid sequence disclosures which are provided in sequence listing.

TECHNICAL FIELD

The invention relates to a method of treatment for states related to inhibition of angiogenesis and endothelial cell proliferation.

TECHNICAL BACKGROUND

CD44 is a transmembrane glycoprotein which functions as cell surface hyaluronic acid (HA) receptor (Aruffo A et al. Cell. 1990 Jun. 29; 61(7):1303-13.). CD44 is involved in cell adhesion on HA, cell migration and HA metabolism.

We have discovered earlier that soluble recombinant CD44 hyaluronic acid binding-domain (CD44-HABD) inhibits angiogenesis in vivo (Päll T et al, Oncogene. 2004 Oct. 14; 23(47):7874-81.). Importantly, CD44-HABD inhibits angiogenesis and endothelial cell proliferation independently of HA-binding (Päll et al, supra). Therefore the inventors hypothesized that CD44 binds to another ligands besides HA on endothelial cells to exert its effects.

Thus, there is a need to find molecules interacting with CD44-HABD, in order to further understanding and control angiogenesis and endothelial cell proliferation, and to provide therapeutic treatment for related states. It is therefore an object of the invention to identify such molecules.

Vimentin is known to be overexpressed in tumor endothelium and targeting vimentin using an antibody has been shown to inhibit angiogenesis both in vivo and in vitro (WO/2007/039255).

SUMMARY OF THE INVENTION

The inventors have now been able to identify one binding partner to CD44, namely vimentin. The inventors have surprisingly found that purified vimentin protein and fragments thereof inhibit endothelial cell proliferation and thereby inhibit angiogenesis.

Thus, in a first aspect, the invention provides a method of treatment for states related to inhibition of angiogenesis and/or endothelial cell proliferation comprising administering an effective amount of vimentin or its derivatives or its fragments, to a subject in need thereof. The vimentin may be in its unmodified and/or phosphorylated form and/or an otherwise modified variant.

In one embodiment, the vimentin has to be at least 95% homologuous to human vimentin amino acid sequence, preferably 100% homologous to SEQ ID NO: 1.

In one embodiment, the vimentin fragment comprises at least amino acids 1-97 of a full length vimentin, preferably the amino-acids 1-97 of human vimentin (SEQ ID NO: 12).

In further embodiments the state to be treated is chosen from the following group: ocular diseases causing blindness or impaired vision, states of chronical inflammation, psoriasis, atherosclerosis, restenosis, cancer growth and metastasis, all forms of cancer diseases and tumours, and hemangioma.

In a second aspect of the invention, the invention provides a method for screening for a binding partner for vimentin, comprising the steps of:
  providing the molecule comprising the vimentin binding domain;
  contacting a potential binding partner to vimentin or its derivative or its fragment; and
  determining the effect of said potential binding partner on vimentin.
  In one embodiment of the second aspect the potential binding partner is chosen from the group comprising peptides and proteins.

In another embodiment a pharmaceutical composition is provided comprising at least one vimentin binding partner according to the method of the second aspect and/or vimentin in mixture or otherwise together with at least one pharmaceutically acceptable carrier or excipient.

In a further embodiment, a method for the treatment of states chosen from ocular diseases causing blindness or impaired vision, states of chronical inflammation, psoriasis, atherosclerosis, restenosis, cancer growth and metastasis, all forms of cancer diseases and tumours, and hemangioma is provided, comprising administering to the patient a pharmaceutical composition according to the above embodiment.

In a third aspect, a medicament comprising vimentin or its derivatives or its fragments is provided. Preferably the vimentin or the fragment has a sequence that is at least 95% homologous to SEQ ID NO: 1. More preferably the sequence is 100% homologous to SEQ ID NO: 1. In other preferable embodiments of the third aspect, the fragment comprises aminoacids 1-97 of a vimentin. In a further embodiment, the fragment comprises the amino acid sequence of SEQ ID NO: 12.

In a fourth aspect, a use of vimentin or its derivatives or its fragments in the manufacture of a medicament for treating states related to inhibition of angiogenesis and/or endothelial cell proliferation is provided.

DEFINITIONS

By "vimentin or its derivatives or its fragments" is meant any molecule, such as an analogue to vimentin, showing a similar or basically the same effect, or a fragment of vimentin, as well as a fusion protein comprising vimentin, or at least an active fragment of vimentin, showing similar or basically the same effect as vimentin. Examples include fusion proteins of vimentin and a fusion partner such as GST, GFP, FLAG, Fc, etc.

By "analogues and recombinant variants" of a molecule comprising vimentin, are meant molecules, such as fusion proteins, comprising vimentin, thereby at least partly exerting essentially the properties of the vimentin.

By "states related to the inhibition of angiogenesis and/or endothelial cell proliferation" are meant such states and diseases, which may be treated or affected by an inhibition of the angiogenesis and/or endothelial cell proliferation.

By "a binding partner" for a molecule comprising vimentin is meant a molecule having affinity for vimentin or mutants thereof.

By "a receptor molecule, or a part of a receptor molecule" is meant a molecule acting as a receptor, or being part of a receptor.

By "a modified variant" is in the context of the invention meant any modification to a normal wild type-molecule, such as deletions, insertions, substitutions, analogs, fragments or recombinant variants thereof.

DETAILED DESCRIPTION OF THE INVENTION

The inventors set out to search for proteins that can interact with CD44-HABD independently of its hyaluronic acid binding capability by using GST-tagged CD44-HABD R41AR78SY79S mutant (CD44-3MUT). The inventors used GST pull-down and peptide mass fingerprinting to identify proteins from human endothelial cells interacting with CD44-3MUT. Here the inventors have discovered that CD44-3MUT binds vimentin expressed on endothelial cell surface. The inventors have found that purified recombinant bacterially expressed vimentin inhibits endothelial cell proliferation in vitro and neoangiogenesis in chick chorio allantoic membrane (CAM). This especially surprising since antibodies against vimentin has been reported to block angiogenesis (WO/2007/039255).

It was recently found that vimentin is secreted by macrophages and vimentin secretion is regulated by pro- and anti-inflammatory cytokines (Mor-Vaknin et al. Nat Cell Biol. 2003 January; 5(1):59-63). Vimentin is an intermediate filament protein expressed in cells of mesodermal origin. Vimentin deficient mice develop and reproduce normally (Colucci-Guyon et al. Cell. 1994 Nov. 18; 79(4):679-94). However, it was found that blood vessel integrity is compromised in vimentin knock-out (KO) mice. Kidneys from vimentin KO mice synthesize less vasodilating agent nitric oxide and renal arteries in these mice are more sensitive to vasoconstricting peptide endothelin. Resulting endothelin/nitric oxide imbalance leads to an impairment of flow-induced vasodilation and causes lethality in pathological conditions, such as reduction of renal mass (Terzi et al. Am J. Pathol. 1997 April; 150(4): 1361-7). Nieminen et al. found that vimentin plays role in lymphocyte adhesion to endothelial cells and transendothelial migration (Nieminen et al. Nat Cell Biol. 2006 February; 8(2):156-62).

The anti-angiogenic activity of vimentin was localized to a N-terminal fragment of vimentin comprising amino-acids 1-97 of vimentin (see example 7). In one embodiment, vimentin fragments comprising this fragment are used for the claimed invention. More preferably, the fragment comprises amino-acids 1-97 of human vimentin having the amino acid sequence of SEQ ID NO: 12.

As shown in FIG. 8, the vimentin protein amino-acid sequence is highly conserved. Therefore, it is likely that vimentin protein from one species would have the same function in another species, e.g. rodent vimentin would give the same effect in humans as in rodents. For instance, in the CAM-assay the human vimentin is effective in chick.

The embodiments listed above may be freely combined with one another. Thus, the details and particulars described above and in the claims apply mutatis mutandis to any other embodiments of the invention. While the invention has been described in relation to certain disclosed embodiments, the skilled person may foresee other embodiments, variations, or combinations which are not specifically mentioned but are nonetheless within the scope of the appended claims.

All references cited herein are hereby incorporated by reference in their entirety.

The expression "comprising" as used herein should be understood to include, but not be limited to, the stated items.

Human vimentin (SEQ ID NO: 1) coding sequence was subcloned into N-terminal His-tag containing bacterial expression vector pET15b. Vimentin expression in bacteria was induced by IPTG and majority of recombinant protein was expressed into inclusion bodies. His-tagged vimentin was purified by using Ni affinity-resin under denaturing conditions. Recombinant protein expression and purification steps were analysed by commassie brilliant blue staining of SDS polyacrylamide gel electrophosesis separated proteins. A, induction of vimentin expression in different E. coli BL21 strains. B, optimisation of vimentin induction temperature in E. coli BL21. Under these conditions vimentin was expressed into inclusion bodies. C, analysis of different purification steps. Arrowhead indicates the position of recombinant vimentin.

Figure 2A:
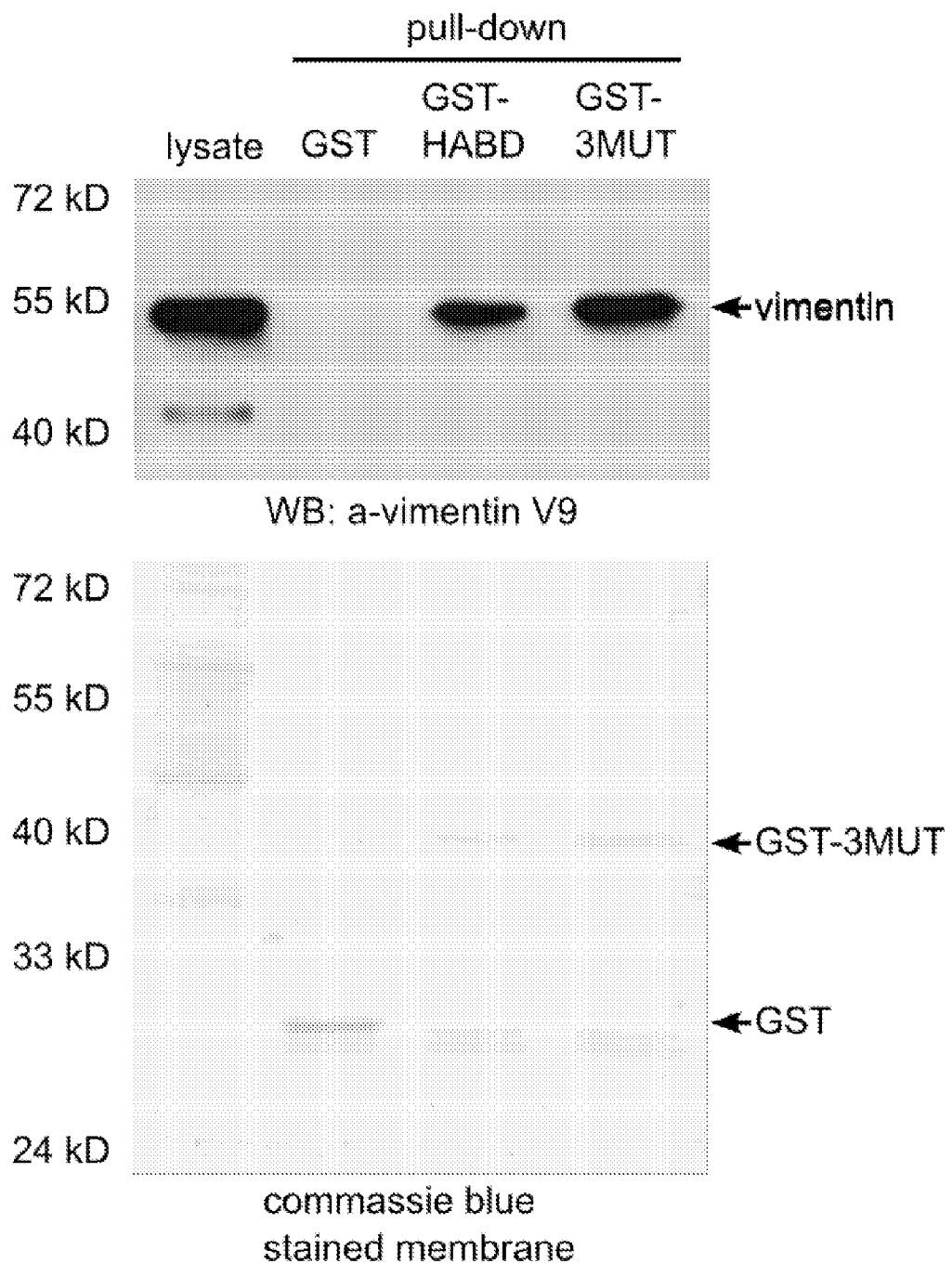

FIGS. 2A-2C. CD44-3MUT Binds Endogenous Vimentin.

GST pull-down was used to identify CD44-HABD binding proteins in HUVEC. A, CD44-HABD and its HA non-binding CD44-3MUT precipitate vimentin from HUVEC lysate. B, CD44-3MUT precipitates 60 kD protein from cell surface biotinylated HUVEC lysate after VEGF stimulation and this pull-down reaction contains vimentin, C. Sequential streptavidin precipitation from GST pull-down eluates was analysed by western blotting with anti-vimentin specific mAb.

Figure 3:
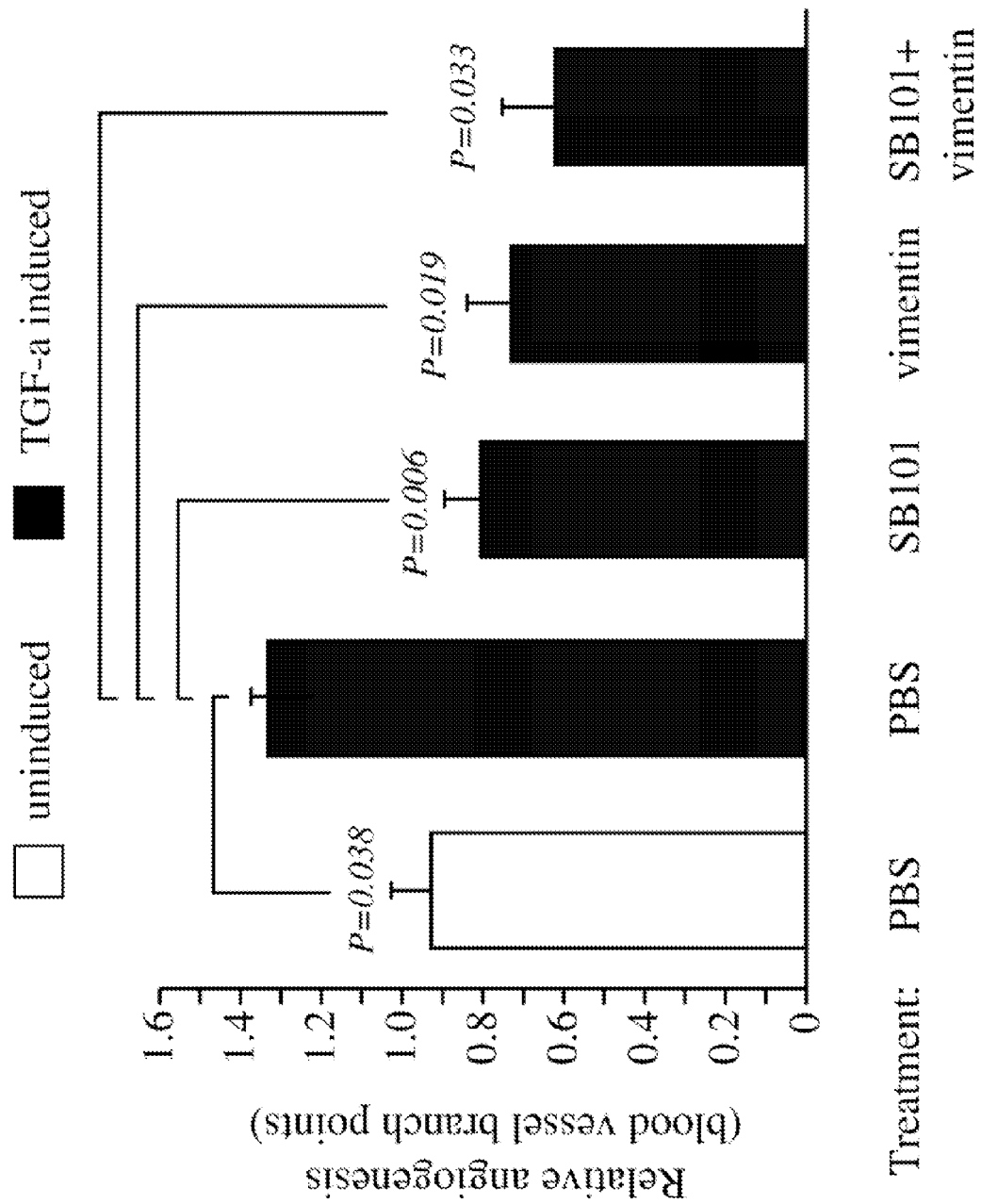

FIG. 3. Vimentin Treatment Blocks Angiogenesis In Vivo in Chick Chorio-Allantoic Membrane.

Angiogenesis was induced in 10-day old chick CAM's under TGF-α soaked paper filter disc, followed by ectopical addition of indicated recombinant proteins or vehicle alone. 72 hours later, filter discs and surrounding CAM was dissected and angiogenesis was quantified by counting blood vessel branch points directly under filter disc. For analysis, normalised data from five independent experiments was pooled. Data show mean±s.e.m. Statistical analysis was performed using unpaired two-tailed Student's t test.

Figure 4:
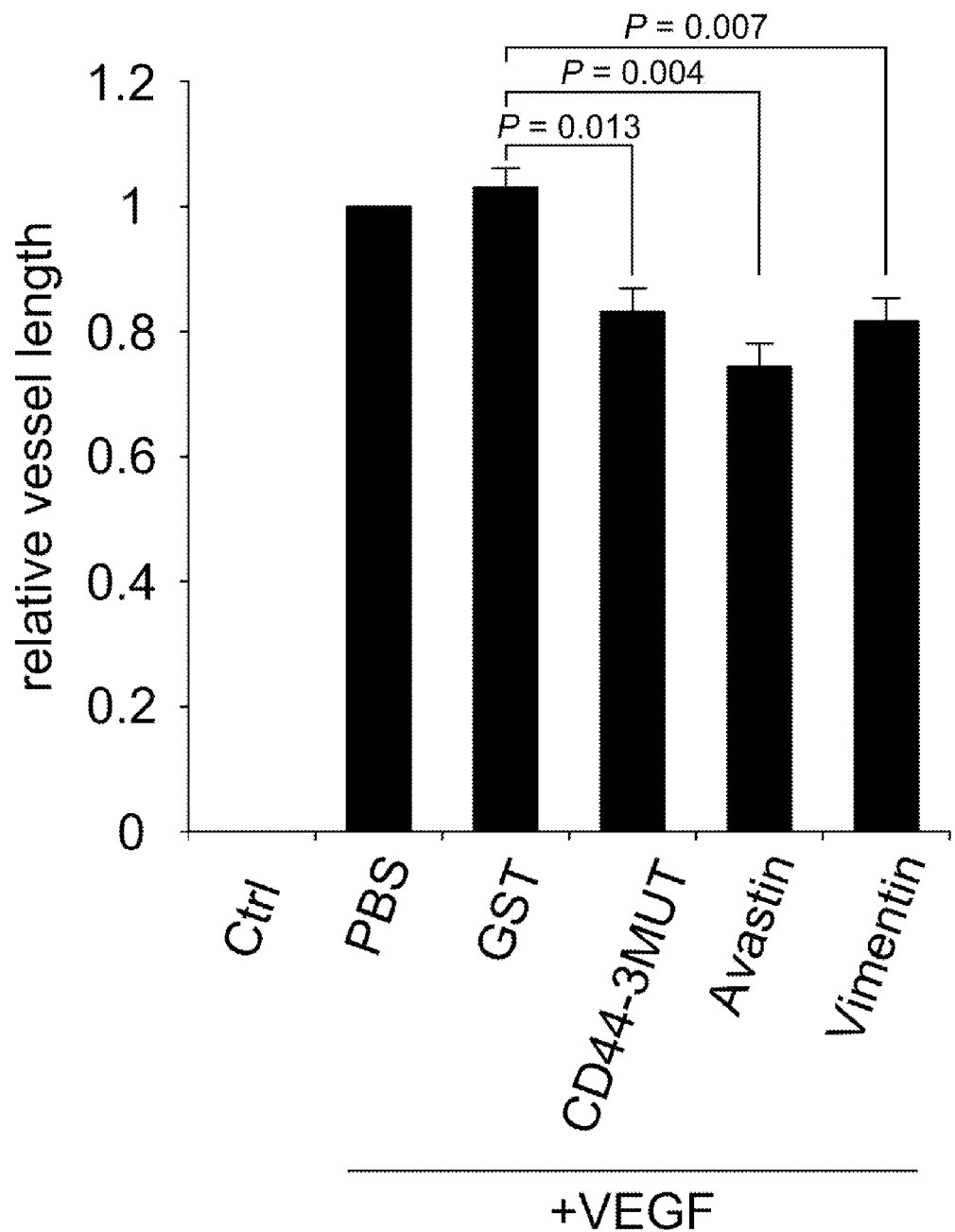

FIG. 4. Vimentin Treatment Inhibits Vessel Growth in Chick Aortic Arch Angiogenesis Assay.

Vessel growth was induced from aortic arch pieces of 14-day old chick embryo by addition of VEGF. Twenty four hours later, organ cultures were fixed and angiogenic response was quantified by measuring the distance of vessel tip from aortic tissue. For statistical analysis, normalised data from three to five experiments were pooled. Data show mean±s.e.m. Statistical analysis was performed using unpaired two-tailed Student's t test.

Figure 5A:
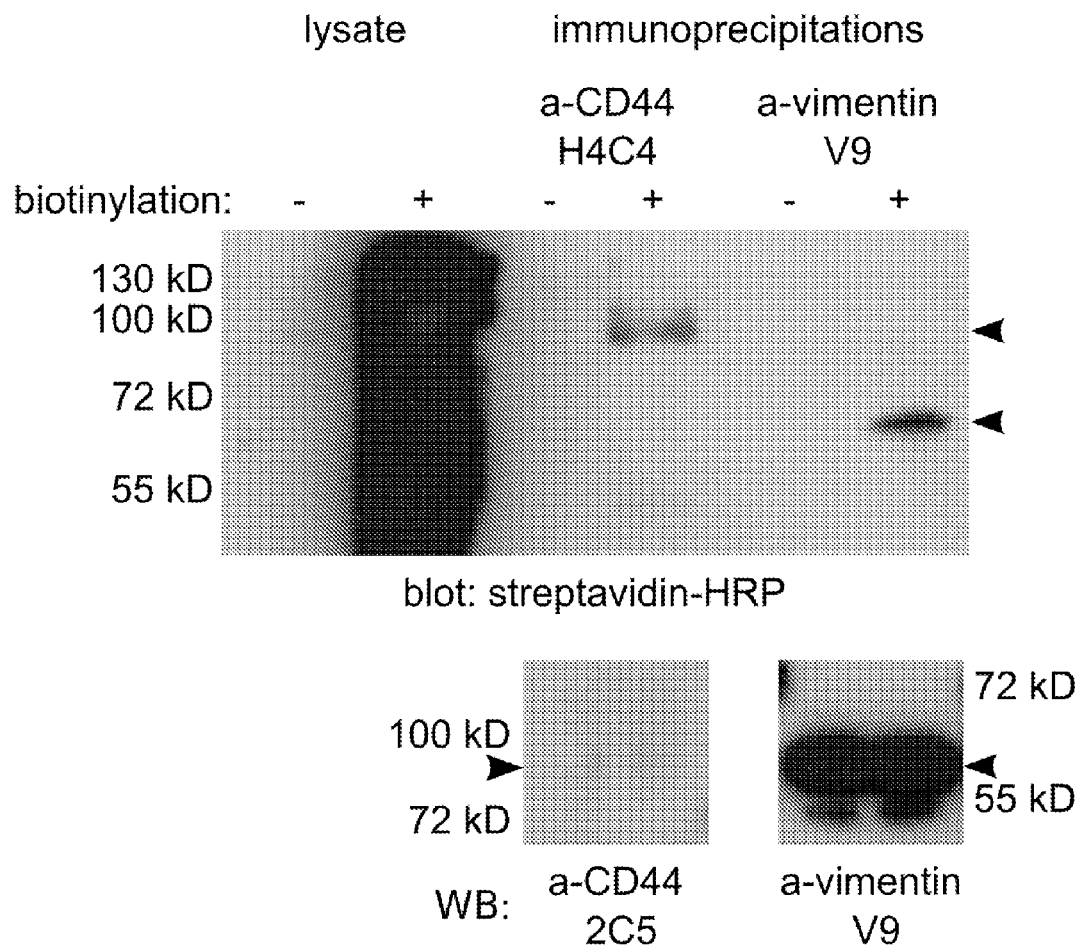

FIGS. 5A and B. Vimentin is Expressed on Endothelial Cell Surface.

A, exponentially growing HUVEC were cell surface biotinylated and anti-vimentin or -CD44 mAb-s were used for immunoprecipitation. Immunoprecipitated proteins were visualised by strepavidin-HRP staining B, trypsinised HUVEC were methanol permeabilised or formaldehyde fixed and stained with anti-vimentin mAb and analysed by FACS.

FIGS. 6 A and B. Recombinant Vimentin Treatment Inhibits Proliferation of Endothelial Cells In Vitro.

Primary HUVEC were either treated 24 h with 10 microg/ml of indicated proteins or left untreated, respectively, and cell cycle profiles were measured. A, cell cycle profiles from anti-BrdU and propidium iodide double staining of HUVEC from representative experiment. B, the proportion of proliferating cells in cell cycle S-phase of recombinant protein treated cells relative to untreated control. Data show mean±s.e.m. Statistical analysis was performed using unpaired two-tailed Student's t test.

Figure 7A:
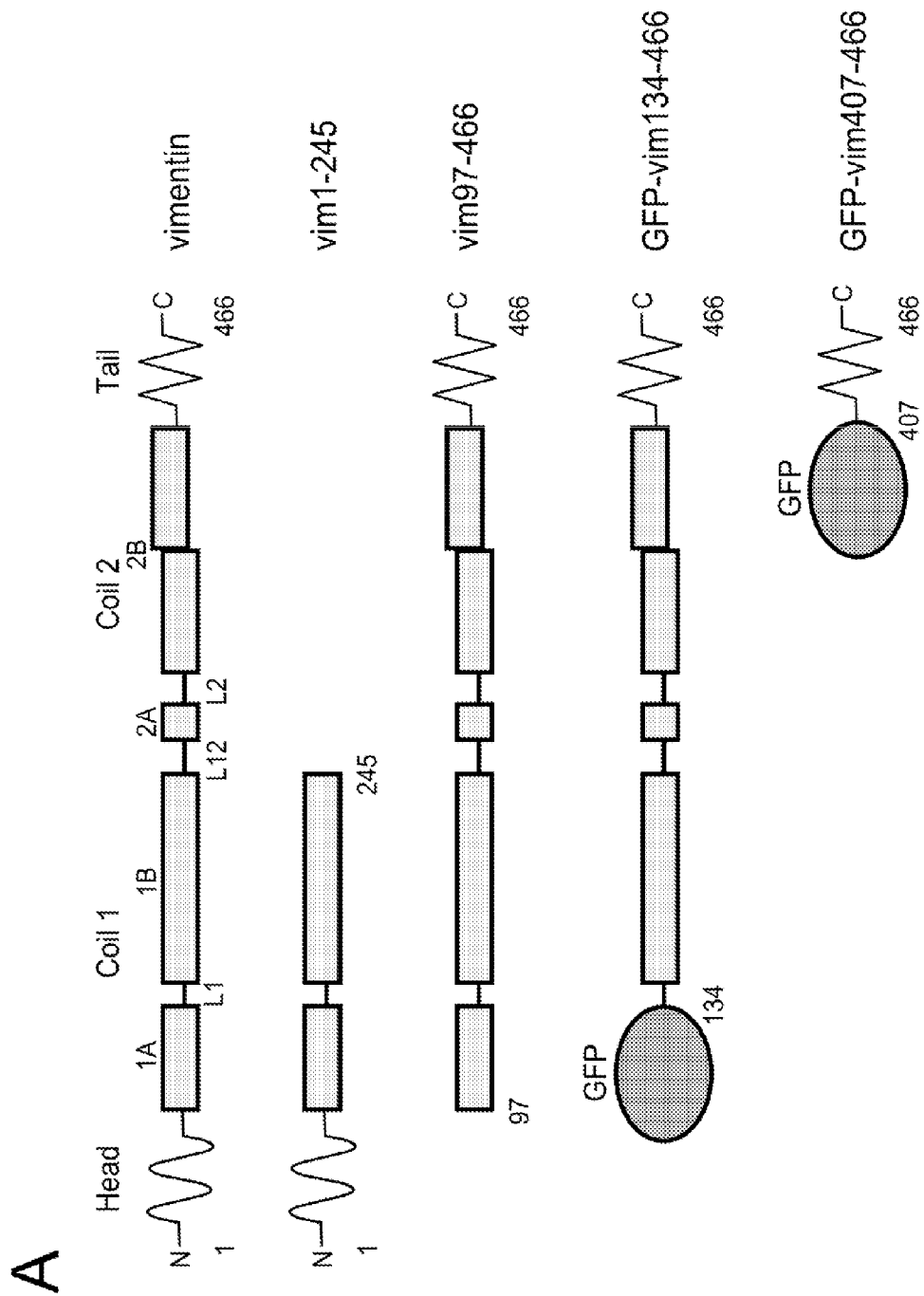

FIGS. 7A and B. CD44-HABD Proteins Bind Vimentin Via its N-Terminal Domain.

Full length vimentin or its deletion mutant constructs were transfected into MCF-7 cells. After incubation cells were lysed and lysate was used in pull-down reaction using GST-tagged CD44-HABD proteins immobilised onto glutathione sepharose beads. After pull-down, beads were washed and bound proteins were eluted. Eluates were analysed on western blot. A, vimentin deletion mutants used in pull-down reactions. B, WB of pull-down reactions from vimentin and its deletion mutant transfected cell lysates.

FIG. 8. BLAST Alignment of Human (SEQ ID NO:1) and Hamster (SEQ ID NO: 14) Vimentin Sequence.

A very high degree of conservation is seen, with 96% identity and 98% similarity with no gaps.

EXAMPLES

The invention will now be further illustrated by means of examples which should not be construed to limit the scope of the invention.

Example 1

Recombinant Vimentin Bacterial Expression and Purification

Figure 1A:
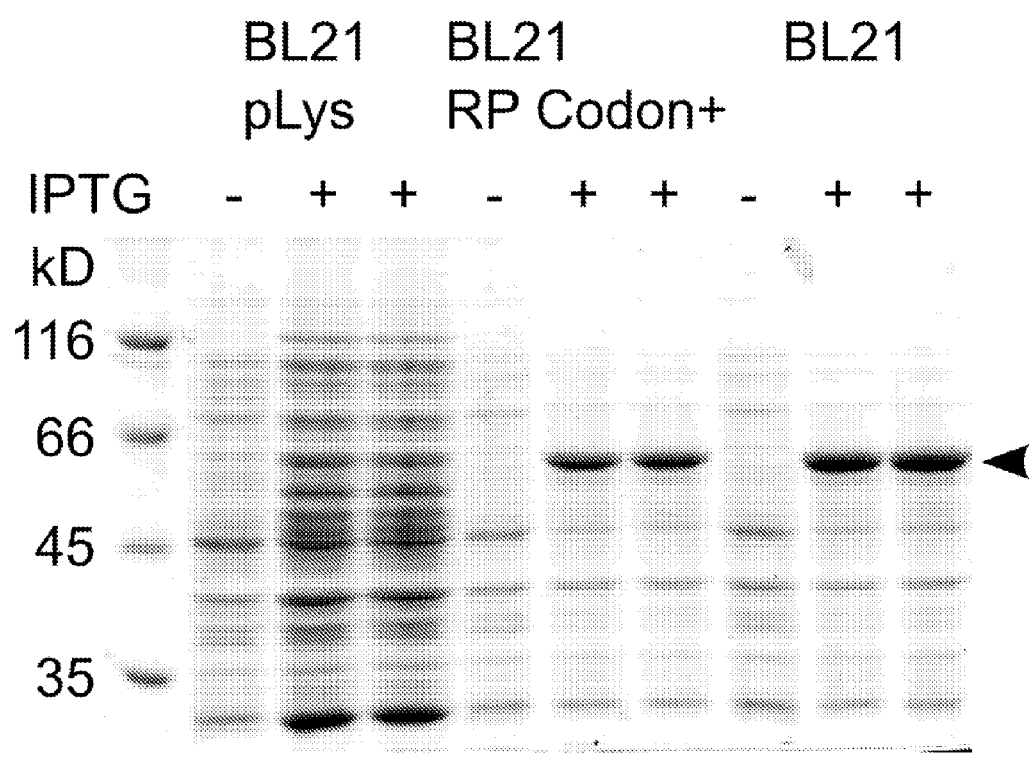
FIGS. 1A-1C. Recombinant Vimentin Bacterial Expression and Purification.
Figure 1B:
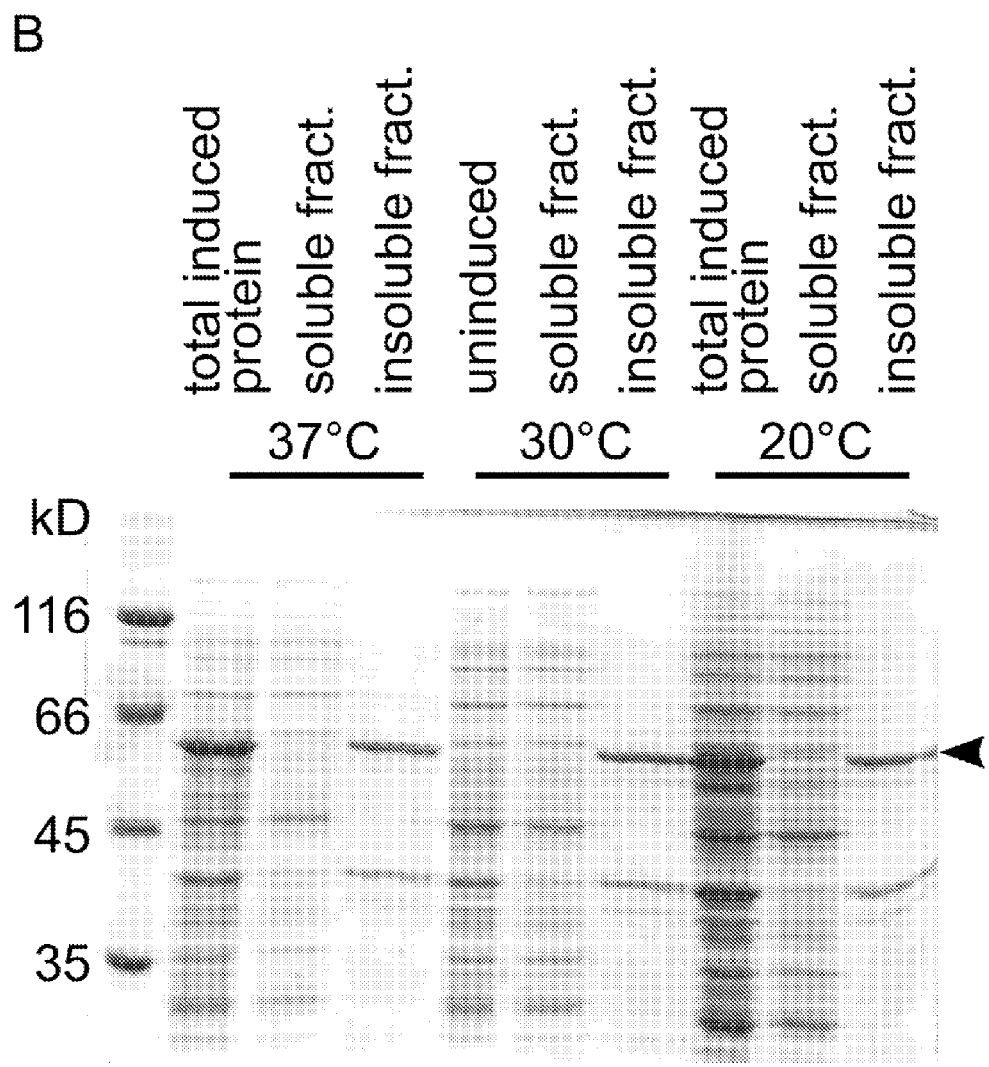
Figure 1C:
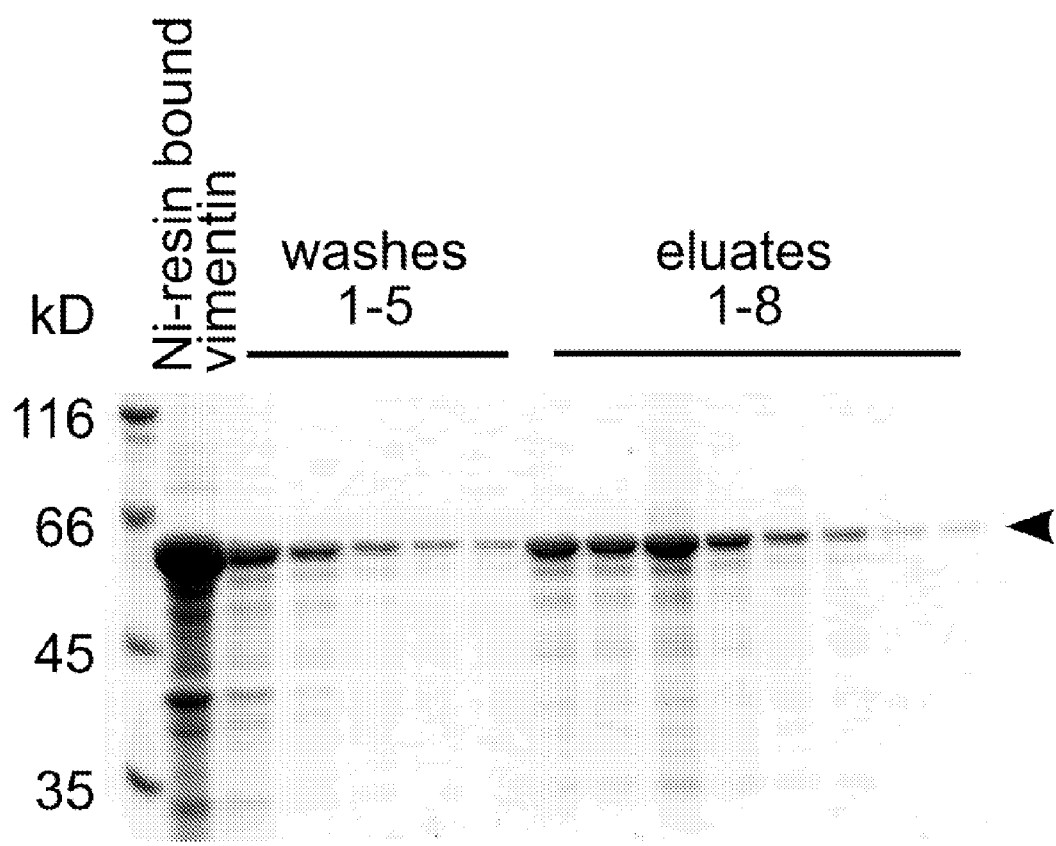

Full length human vimentin cDNA clone IRATp970E0267D (RZPD, Berlin, Germany) coding for human vimentin (SEQ ID NO: 1) was used to create N-terminal 6×His containing vimentin bacterial expression construct in pET15b vector. Briefly, two step subcloning was used, first XhoI/BamHI restriction fragment from C-terminal half of original vimentin cDNA clone was inserted into pET15b. Then 400 bp fragment starting from ATG until to unique XhoI site in vimentin cDNA was PCR amplified by using oligos NdeFW 5'GAACATATGTCCACCAGGTC-CGTGTCC 3' (SEQ ID NO: 2) and XhoRev 5' GCGACT-TGCCTTGGCCCTTGAGCTCC 3' (SEQ ID NO: 3) and inserted into NdeI/XhoI site of vimentin C-terminal half containing pET15b vector. The correctness of resulting vimentin expression construct was sequence verified. Vimentin expression was induced in *E. coli* BL21(DE3) strain 3 hours at 30° C. in TB media with 1 mM IPTG at $OD_{600}$=0.7 (FIG. 1A). Bacteria were pelleted by centrifugation 10 min 5000 rpm at 4° C. in Sorvall RC 5C Plus centrifuge GSA rotor and pellet was resuspended in 30 ml PBS per 1 L of culture. After resuspension, bacteria were lysed by using 1 mg/ml lysozyme 30 min at 4° C., followed by three cycles of freezing and thawing. After freeze-thaw cycles lysate was sonicated. Majority of the expressed vimentin resulted in inclusion bodies (FIG. 1B). Inclusion bodies were pelleted by centrifugation 30 min 15000 rpm in Sorvall RC 5C Plus centrifuge in SS-34 rotor. Inclusion body pellet was then washed twice with buffer containing 50 mM Tris pH=8.0, 100 mM NaCl, 1% Triton X-100, 1 M urea, then twice with buffer containing 50 mM Tris pH=8.0, 100 mM NaCl, 1% Triton X-100 and then once with 50 mM Tris pH=8.0, 100 mM NaCl. After washes inclusion bodies were solubilised over-night (ON) with constant shaking in 8 M urea in 50 mM Tris pH=8.0, 100 mM NaCl at room temperature. Ni Cam resin beads (Sigma-Aldrich) were washed according to manufacturers protocol and beads were then incubated with vimentin inclusion bodies solution 1 hour at 4° C. Then beads were washed 5 times in 10 ml vol wash buffer containing 20 mM Tris pH=8.0, 6 M urea, 100 mM NaCl, 20 mM imidazole. Bound proteins were eluted from beads in 0.5 ml vol with elution buffer containing 20 mM Tris pH=6.3, 6 M urea, 100 mM NaCl, 250 mM imidazole (FIG. 1C). Eluates were then pooled and dialysed sequentially against 6 M, 4 M, 2 M, 1 M and 0.5 M urea in 10 mM Tris pH=8 buffer in 100 times volume excess, at least 2 h each step and followed by ON dialysis in 10 mM Tris pH=8.0. Then protein eluates were dialysed 3 times in 10 mM phosphate buffer pH=7.4 with sequential incubation times 2 h, 4 h and ON.

Example 2

Cell Surface Expressed Vimentin Binds Recombinant CD44-HABD R41AR78SY79S (CD44-3MUT)

To discover endothelial protein targets for previously described angiogenesis inhibiting protein CD44-3MUT (SEQ ID NO: 13) (Päll T et al, Oncogene. 2004 Oct. 14; 23(47):7874-81.), we performed GST pull-down from HUVEC membrane lysates with GST tagged CD44-3MUT (GST-3MUT). For preparation of membrane fractions, adherent cells were washed with ice-cold PBS and lysed in 50 mM Tris pH 8.0, containing protease inhibitor cocktail (Complete, Roche Applied Science, Mannheim, Germany). Insoluble material was pelleted by centrifugation at 14000 rpm 30 min. 4° C. Pellet was then solubilised in buffer containing 2% CHAPS, 50 mM Tris pH 8.0, 50 mM NaCl, protease inhibitor cocktail and centrifuged 14000 rpm 10 min. at 4° C. Resulting lysate was precleared by incubation 2 h with 20 µg glutathione S-transferase immobilised onto 25 µl Glutathione Sepharose 4 Fast Flow beads (Amersham Biosciences, Uppsala, Sweden) at 4° C. After preclearing, lysate was incubated over-night at 4° C. with 10 µg GST, GST-HABD or GST-3MUT proteins immobilised onto 25 µl glutathione sepharose beads. After incubation beads were pelleted in cold centrifuge and washed 4 times with 200 µl buffer containing 50 mM Tris pH 8.0, 150 mM NaCl, protease inhibitor cocktail. Bound proteins were eluted 5 times with 25 µl 20 mM reduced glutathione, 50 mM Tris pH 8.0. Eluates were pooled and eluted proteins were precipitated by addition of 1 vol. 20% TCA and centrifugation at 14000 rpm 30 min 4° C., precipitate was then washed with cold acetone and aspirated dry. For silver staining and subsequent mass spectrometric analysis, protein samples were solubilised in 1×SDS sample buffer containing 50 mM DTT in final concentration instead of 2-mercaptoethanol and alkylated by addition ⅒ vol of freshly prepared 1 M iodoacetamide and incubation 30 min in dark and cold. Silver staining of proteins separated by SDS-PAGE was performed as described in by Shevchenko et al. (Biochem Soc Trans. 1996 August; 24(3):893-6).

Silver staining of pull-down reactions separated by SDS-PAGE revealed that approximately 60 kD size protein band coprecipitated with GST-3MUT compared to GST alone. This protein band was analysed by peptide mass fingerprinting of trypsinolytic fragments and contained vimentin. To confirm that CD44-HABD proteins coprecipitate vimentin, we used vimentin-specific monoclonal antibody V9 to analyse CD44-HABD GST pull-down reactions by western blotting and found that GST-3MUT as well as GST-HABD coprecipitate vimentin from endothelial cell membrane lysates (FIG. 2A).

To study if SB101 (synonymous with CD44-3MUT) binds cell surface expressed vimentin we performed GST pull-down from surface biotinylated HUVEC lysate. HUVEC were serum starved for 6 h in 0.5% FBS containing media and then induced with 10 ng/ml $VEGF_{165}$ 1 h at 37° C. or left uninduced. After growth factor induction, cells were surface biotinylated on tissue culture plate with 5 ml EZ Link sulfo-NHS-SS-biotin (Pierce, Rockford, Ill., USA) 1 mM in PBS, 0.1% $NaN_3$. After biotinylation cells were washed 3 times with PBS-100 mM glycine. Then cells were lysed with 2% CHAPS, 50 mM Tris pH 8.0, protease inhibitor cocktail (Complete, Roche Applied Science, Penzberg, Germany) and incubated 15 min on ice, unsoluble material was pelleted by centrifugation in microcentrifuge 14000 rpm 10 min at 4° C. After centrifugation supernatant was aspirated and pellet was redissolved in 2% CHAPS, 50 mM Tris pH 8.0, protease inhibitor cocktail containing buffer, followed by centrifugation in microcentrifuge 14000 rpm 10 min at 4° C. Supernatant was saved for GST pull-down. For pull-down glutathione sepharose 4 fast flow beads (GE Healthcare Bio-Sciences, Uppsala, Sweden) were preincubated with 10 µg GST-SB101 or GST in 0.5 ml vol PBS. The biotinylated membrane lysate was precleared by incubation 2 h at 4° C. with constant end-over-end rotation by using GST-coupled glutathione beads. Precleared lysate (0.3 ml vol per reaction) was used to pull down GST-SB101 binding proteins, GST-bound glutathione beads were used as control, pull-downs were incubated 2 h at 4° C. with rotation. After pull-down reactions, beads were washed 4 times with 0.4 ml vol wash buffer (50 mM Tris pH 8.0, 150 mM NaCl, protease inhibitor cocktail). Bound proteins were eluted with 20 mM reduced glutathione in 50 mM Tris pH 8.0. Eluates were pooled and volume adjusted to 0.5 ml so that solution contained in final concentration 50 mM Tris pH 8.0, 50 mM NaCl, 4 mM reduced glutathione and 1× protease inhibitor cocktail. After SDS PAGE pull-down reactions were analysed by western blotting with HRP-conjugated strepavidin (FIG. 2B). Results show that SB101 pulls down approximately 60 kDa size biotinylated protein. This process is dependent on growth factor stimulation as can be induced by VEGF.

Next, to verify that SB101 precipitated biotinylated protein band contains vimentin we performed sequential strepavidin precipitation from GST pull-down eluates. For this 25 µl of prewashed strepavidin-agarose resin (Sigma, St. Louis, Mo., USA) was added into GST pull-down eluate and incubated 2 h at 4° C. with rotation. After incubation strepavidin beads were washed in sequence 2 times with 50 mM Tris pH 8.0, 150 mM NaCl, 2 times with 0.1 M Na-borate pH 8.5, 2 times with 0.1 M Na-acetate pH 4.5 and finally with 50 mM Tris pH 8.0, 150 mM NaCl. Bound proteins were then eluted from strepavidin beads with 1×SDS sample buffer containing 50 mM DTT instead of 2-mercaptoethanol 30 min at 50° C. followed by 3 min at 95° C. Then samples were analysed by western blotting with anti-vimentin specific mAb V9.

The result shows that SB101 binds in response to VEGF stimulation endogenous cell surface expressed vimentin (FIG. 2C).

Example 3

Recombinant Vimentin Inhibits Angiogenesis in Chick Chorio-Allantoic Membrane 10-day-old chick embryos were prepared as described in (Brooks et al. Methods Mol. Biol. 1999; 129:257-69). For angiogenesis assay, filter discs soaked with 100 ng/ml TGF-α were placed on CAM's, followed by daily ectopical addition of 10 µg of vimentin, CD44-3MUT or PBS as control (n=6-8 per group). After 72 h, filter discs and the surrounding CAM tissue were dissected and angiogenesis quantified in a dissection microscope. Angiogenesis was assessed as the number of blood vessel branch points within the CAM area directly under the filter discs. Vimentin or CD44-3MUT but not GST treatment completely abolished the angiogenic effect of TGF-α (FIG. 3), indicating that soluble vimentin blocks angiogenesis as effectively as previously described angiogenesis inhibitor CD44-3MUT.

Example 4

Recombinant Vimentin Inhibits Vessel Growth in Chick Aortic Arch Angiogenesis Assay Aortic arches were dissected from 14-day old chick embryos. Vessels were dissected free from connective tissue and cut into approximately 1 mm pieces. Then were aortic fragments embedded into collagen type I gel (Upstate, Lake Placid, N.Y., USA) with final concentration 2 mg/ml in M199 media supplemented with 4 mM L-glutamine, 25 mM HEPES, pH of the gel was adjusted to neutral with 10 N NaOH. Angiogenesis was induced by addition of 20 ng/ml VEGF165 into gel. Recombinant proteins in PBS were added at final concentration 10 µg/ml or vehicle alone for control treatment. For experiment, 35 µl premixed gel was pipetted into 96-well and gelled 20 min at 37° C. to form a bed for aortic tissue, then piece aortic arch was put onto gel and covered with 65 µl of premixed gel. Plate was incubated 24 h at 37° C. with 5% CO2. At the end of incubation gel was fixed by addition of 100 µl of 10% formaldehyde in PBS and incubated 48 h at room temperature.

For quantitation photomicrographs were taken with Zeiss Axiovert 200M microscope equipped with Zeiss A-Plan 10× objective and AxioCam MRc camera. Quantitation was done on DIC images with AxioVision 4.5 software by measuring the distance of vessel tip from aortic arch tissue fragment.

Results show that in the absence of VEGF there is no neovessel outgrowth from aortic arch tissue in collagen type I gel and only in response to VEGF induction the robust vessel growth occurs (FIG. 4). When recombinant bacterially expressed vimentin was added into gel the average vessel length was significantly reduced compared to GST control treatment. In these assays vimentin effect was comparable to effects of SB101 (synonymous with CD44-3MUT) and avastin.

Example 5

Vimentin is Expressed on Endothelial Cell Surface

We performed biotinylation of cell-surface proteins on adherent live HUVEC by using EZ-Link sulfo-NHS-LC-biotin reagent and protocol (Pierce, Rockford, Ill., USA), followed by immunoprecipitation of vimentin from cell lysates by using anti-vimentin mouse mAb V9 (Santa Cruz Biotechnology) or CD44 with mouse mAb H4C4 (Developmental Studies Hybridoma Bank) as positive control for cell surface expressed protein. Biotinylated immunoprecipitated proteins were detected in blot by HRP-conjugated streptavidin (Santa Cruz Biotechnology, Santa Cruz, Calif., USA). As shown in FIG. 5A, vimentin antibody V9 immunoprecipitates from HUVEC lysate biotinylated protein in range of approximately 60 kD, whereas anti-CD44 antibody H4C4 immunoprecipitates biotinylated protein in between 72 and 100 kD size range, which corresponds to expected size of endothelial CD44.

Figure 5B:
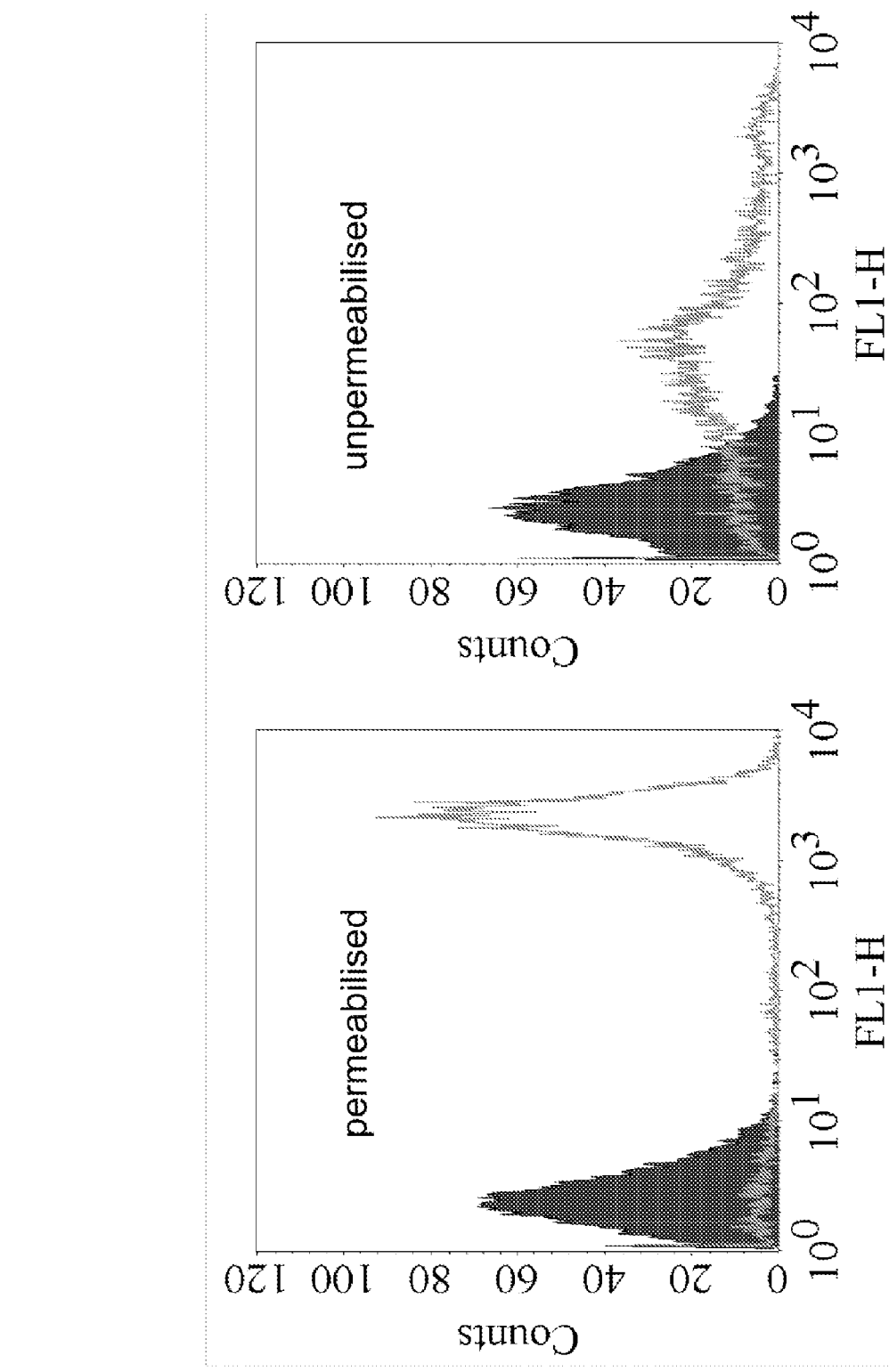

Then we used FACS analysis of anti-vimentin stained permeabilised and non-permeabilised HUVEC to characterize vimentin cell surface expression. FACS analysis for cytoplasmic vimentin of HUVEC permeabilised 10 min in −20° C. methanol shows homogeneous high-intensity staining population (FIG. 5B). When nonpermeabilised cells fixed 10 min at room temperature in 4% formaldehyde/PBS were analysed less intensively staining heterogeneous cell population is apparent.

Example 6

Recombinant Vimentin Inhibits Human Vascular Endothelial Cell (HUVEC) Proliferation In Vitro Primary human umbilical vein endothelial cells (HUVEC) were maintained in M199 basal media supplemented with 20% FBS, 10 mM HEPES, 4 mM L-glutamine, 50 µg/ml heparin and 30 µg/ml endothelial cell growth supplement (Upstate, Temecula, Calif., USA) and penitsillin-streptomycin. Only cells from up to 7$^{th}$ passage were used.

Figure 6A:
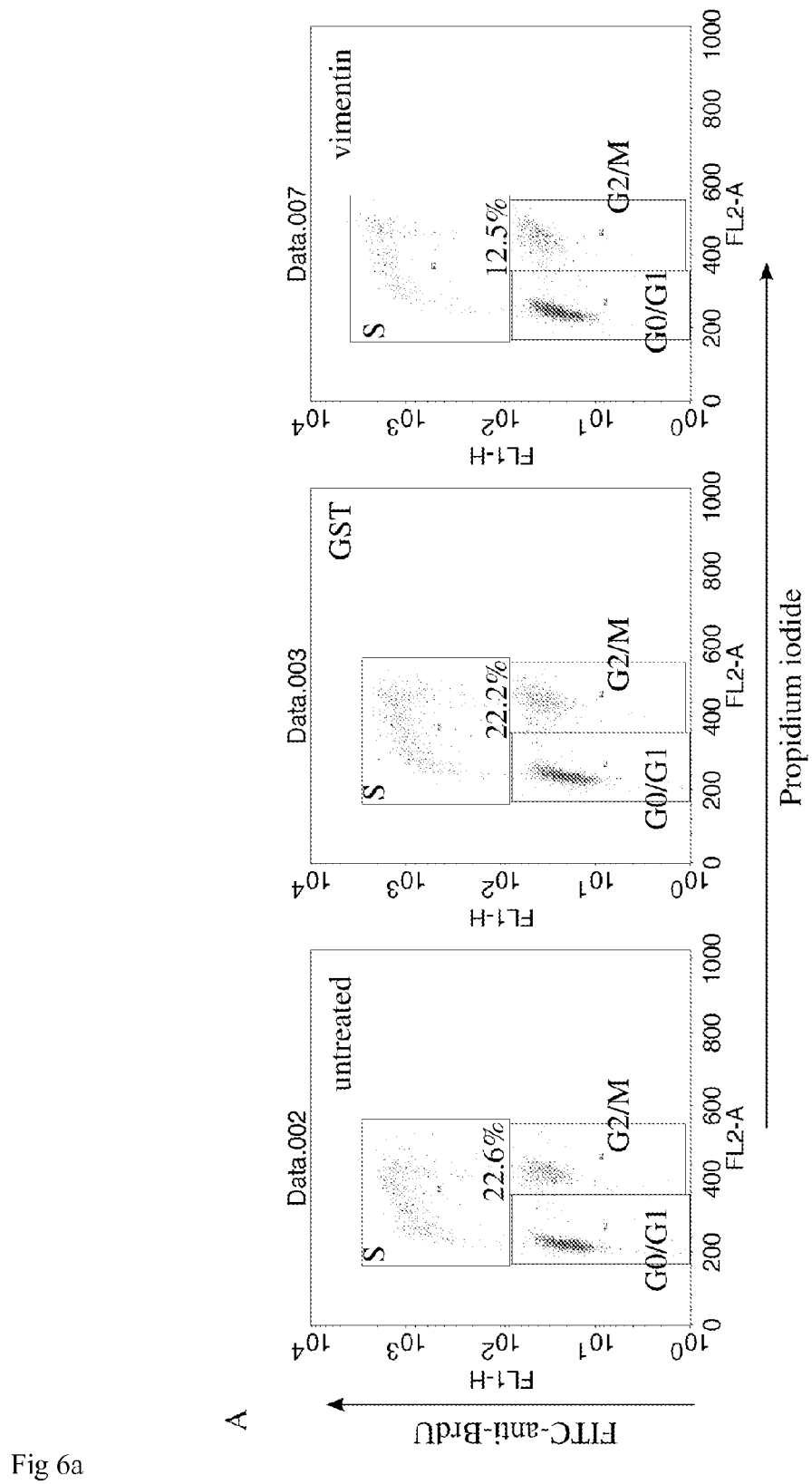

For cell cycle analysis, 60-80% confluent cells were incubated in 10% FBS containing media for 24 h in the presence of recombinant proteins at 10 µg/ml concentration. After 24 h, cells were pulsed with 30 µg/ml bromodeoxyuridine for 60 min, harvested and fixed in ice-cold ethanol. Cells were then stained for BrdU with anti-BrdU mAb G3G4 (Developmental Studies Hybridoma Bank, University of Iowa, Iowa, USA) followed by a FITC-conjugated goat anti-mouse antibody (Jackson Immunoresearch, West Grove, Pa., USA) in parallel staining with propidium iodide. The cell cycle distribution was then analysed with a FACS Calibur flow cytometer and Cellquest software (Becton Dickinson, Franklin Lakes, N.J., USA) after plotting FITC-content vs. propidium iodide (FIG. 6a).

Figure 6B:
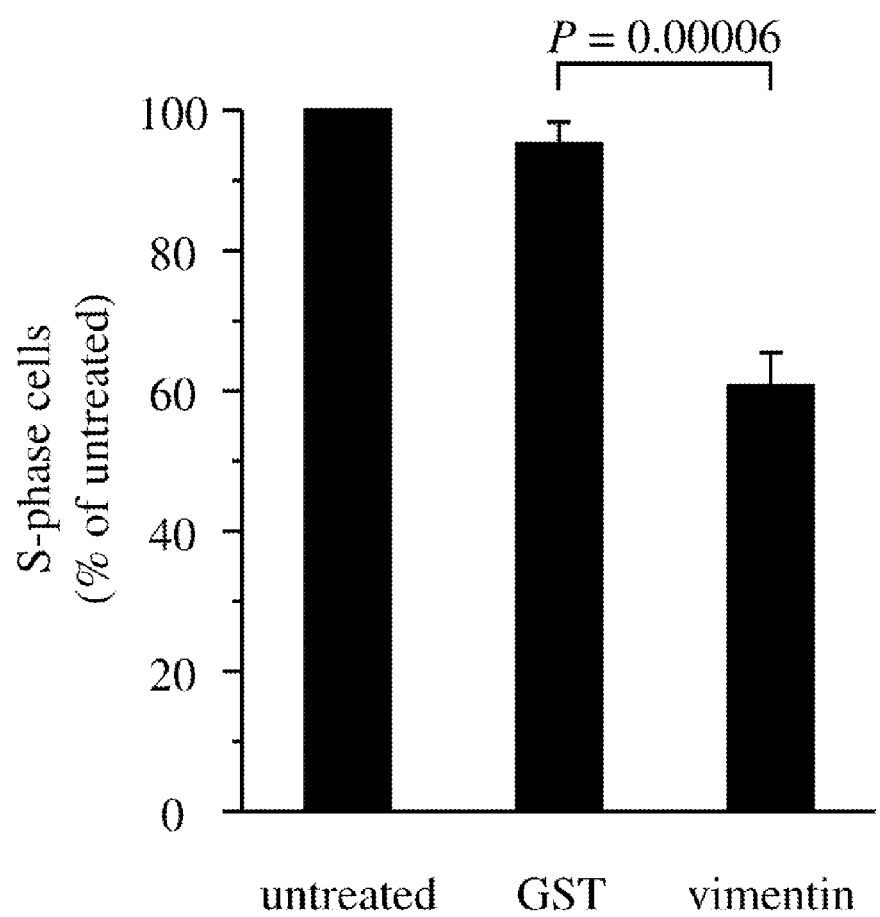

The results from cell cycle analysis of untreated HUVEC population show that the proportion of proliferating cells in S-phase is (mean±s.e.m.) 21.5±2.8% (n=10), whereas S-phase population in GST-control treated cells is 21.9±2.6% (n=7). HUVEC treatment with soluble recombinant vimentin reduces the amount of S-phase cells by 33% to 14.5±1.9% (unpaired two-tailed Student's t test, GST vs. vimentin, P=0.00006; n=6). For statistical analysis the proportion of S-phase cells in GST and vimentin treatment groups was normalised within each experiment to untreated control; as shown in FIG. 6b.

Example 7

Vimentin Binds to CD44-3MUT Via its N-Terminal Filament Head Domain

For creation of full length vimentin mammalian expression construct, human vimentin cDNA was PCR amplified using oligos 5'-CCGAATTCATGTCCAGGTCCGTGTCC-3' (SEQ ID NO: 4) and 5'-GGCCGCGGTTCAAGGTCATCGTGATG-3' (SEQ ID NO: 5) containing EcoRI or SacII restriction site respectively. Vimentin fragment was inserted into EcoRI/SacII site of pcDNA3.1/MycHis B vector (VIM-pcDNA; Invitrogen).

Vimentin deletion mutant containing aa 1-245 of SEQ ID NO: 1 (VIM_1-245; FIG. 7A) was PCR amplified from human vimentin cDNA using oligo pair 5'-CCGAATTCATGTCCAGGTCCGTGTCC-3' (SEQ ID NO: 6) and 5'-GTGCGGCCGCCCAGCTCCTGGATTTCCTC-3' (SEQ ID NO: 7) and deletion mutant containing aa 97-466 of SEQ ID NO: 1 (VIM_97-466) using oligo pair 5'-CAGAATTCATGAACACCCGCACCAACGAG-3' (SEQ ID NO: 8) 5'-CAGCGGCCGCCTTCAAGGTCATCGTGATG-3' (SEQ ID NO: 9), both pairs contain EcoRI restriction site in forward oligo and NotI site in reverse oligo. PCR fragments were inserted into EcoRI/NotI site of pcDNA3.1/MycHis B vector.

Vimentin deletion mutant containing aa 407-466 of SEQ ID NO: 1 (VIM_407-466) was PCR amplified from human vimentin cDNA by using oligos 5'-GAGTGGAATTCGAGGAGAGCAGG-3' (SEQ ID NO: 10) and 5'-GCCGTCGACATTGCTGCACTGAGTGTGTGC-3' (SEQ ID NO: 11), containing EcoRI or SalI site respectively. Vimentin fragment was inserted into EcoRI/SalI site of pEGFP-C2 vector (Clontech). Vimentin deletion mutant containing aa 134-466 of SEQ ID NO: 1 (VIM_134-466) was created by inserting XhoI/BamHI restriction fragment from full length human vimentin containing pEGFP-C2 vector (VIM-pEGFP) into pEGFP-C3 vector. pEGFP-VIM construct was created by cutting full-length vimentin from VIM-pcDNA with EcoRI and SacII restrictases and inserting it into pEGFP-C2 vector.

CD44-3MUT binding of vimentin deletion mutants was tested using GST pull-down from cell lysates. MCF-7 cells were transfected with vimentin deletion-constructs on 15 cm cell culture plates using 20 µg DNA with polyethyleneimine (PEI; DNA and PEI were used in ratio 1:2). Transfected cells were incubated at 37° C. for 72 h. Thereafter, adherent cells were washed once with cold PBS and lysed in 2 ml of lysis buffer containing 50 mM Tris pH 8.0, 50 mM NaCl, 2% CHAPS and protease inhibitor cocktail (Roche). For removal of insoluble material the lysates were centrifuged 14000 rpm 30 min at 4° C. Resulting lysates were used in GST pull-down. For pull-down 10 µg GST, GST-HABD or GST-3MUT were immobilised onto glutathione sepharose 4 fast flow beads (GE Healthcare) in 0.5 ml of PBS. Cell lysates were precleared by incubating the lysates with GST-coupled glutathione beads for 2 h at 4° C. with continuous rotation. After preclearing, the lysates (0.6 vol per reaction) were incubated over-night at 4° C. with GST, GST-HABD or GST-3MUT proteins immobilised onto 25 µl glutathione sepharose beads. After pull-down reactions, beads were washed 4 times with 0.3 ml vol wash buffer containing 50 mM Tris pH 8.0, 150 mM NaCl and protease inhibitor cocktail. Bound proteins were eluted 3 times with 25 µl volume elution buffer 20 mM reduced glutathione, 50 mM Tris pH 8.0. Eluates were pooled and after SDS PAAG pull-down reactions were analysed by western blotting with anti-His specific pAb (H-15) (Santa Cruz Biotechnology) or anti-vimentin specific pAb (Genway).

Figure 7B:
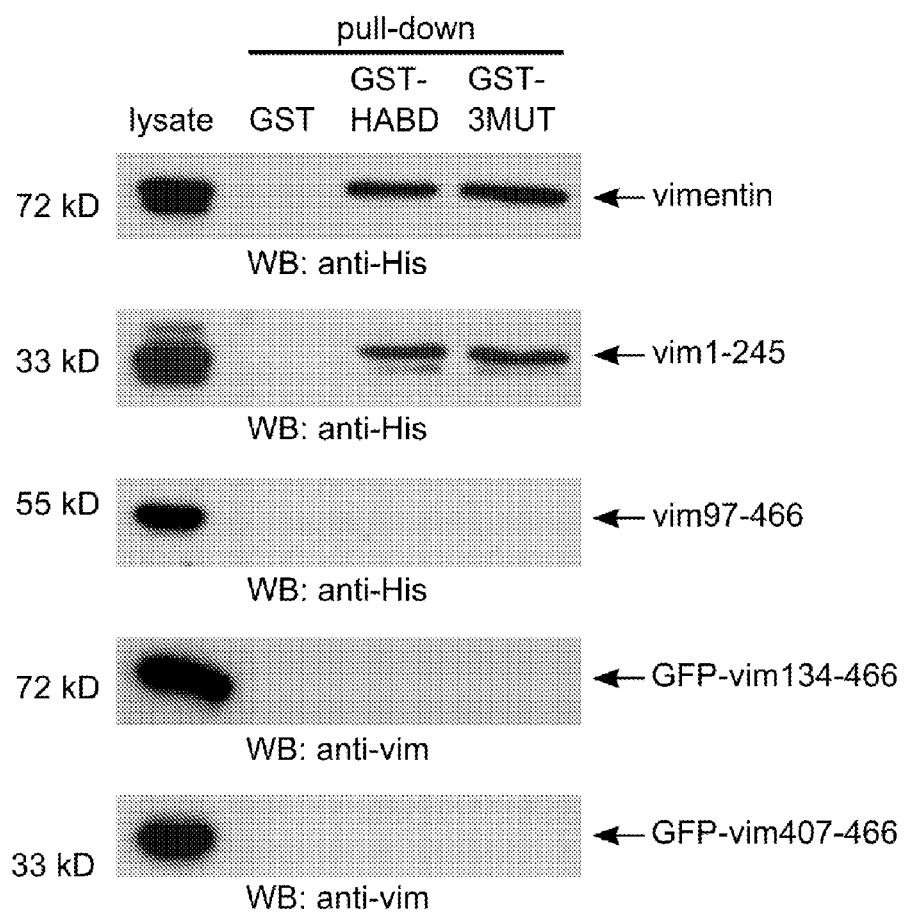

WB of pull-down reactions shows that in addition to full length vimentin, GST-HABD and GST-3MUT coprecipitated from cell lysates VIM_1-245 mutant (FIG. 7B), whereas VIM 97-466, VIM_134-466 or VIM_407-466 did not show any coprecipitation with CD44-HABD proteins. Together, these data indicate that CD44-HABD proteins bind vimentin via its N-terminal aa 1-97 (e.g. SEQ ID NO: 12) containing conserved filament head domain.

The invention claimed is:

1. A method to manufacture a medicament for inhibition of angiogenesis or endothelial cell proliferation, said method comprising the use of vimentin according to SEQ ID NO:1, or a fragment thereof comprising SEQ ID NO:12 in the medicament.

2. The method of claim 1, wherein the vimentin consists of SEQ ID NO:1.

3. The method of claim 1, wherein the vimentin fragment consists of SEQ ID NO:12.

4. A medicament for inhibition of either angiogenesis or endothelial cell proliferation, said medicament comprising a fragment of vimentin, wherein said fragment comprises SEQ ID NO:12.

5. A pharmaceutical composition for treating states requiring inhibition of either angiogenesis or endothelial cell proliferation in a human, said composition comprising the vimentin of SEQ ID NO:1 or a fragment thereof comprising SEQ ID NO:12, in a mixture or otherwise together with at least one pharmaceutically acceptable carrier or excipient.

6. A method for the treatment of states requiring inhibition of either angiogenesis or endothelial cell proliferation in a human, the method comprising administering to the patient a pharmaceutical composition according to claim 5.

7. A method of inhibiting angiogenesis and endothelial cell proliferation, said method comprising using the vimentin of SEQ ID NO:1, a fragment thereof comprising SEQ ID NO:12, or a vimentin which is at least 95% identical to SEQ ID NO:1.

8. The method according to claim 7, wherein the vimentin is in its unmodified or phosphorylated form.

9. The method according to claim 7, wherein the amino acid sequence of the vimentin is SEQ ID NO:1.

10. The method according to claim 7, wherein the vimentin fragment is SEQ ID NO:12.

11. The method according to claim 7, wherein the method is used for treating a state requiring inhibition of either angiogenesis or endothelial cell proliferation.

12. The method of claim 11, wherein the state is a tumorous cancer.

13. The method of claim 7, wherein the method is to inhibit angiogenesis and endothelial cell proliferation in vitro.

* * * * *

SEQUENCE LISTING

<160> NUMBER OF SEQ ID NOS: 14

<210> SEQ ID NO 1
<211> LENGTH: 464
<212> TYPE: PRT
<213> ORGANISM: Homo sapiens

<400> SEQUENCE: 1

-continued

```
Met Ser Thr Arg Ser Val Ser Ser Ser Tyr Arg Arg Asn Phe Gly
1               5                   10                  15

Gly Pro Gly Thr Ala Ser Arg Pro Ser Ser Ala Ser Tyr Val Thr
                20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Pro Gly Gly Val Tyr Ala Thr Arg
50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
            115                 120                 125

Lys Ile Leu Leu Ala Glu Leu Glu Gln Leu Lys Gly Gln Gly Lys Ser
            130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
            195                 200                 205

Asp Phe Asp Asn Ala Ser Leu Ala Arg Leu Asp Leu Glu Arg Lys Val
210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
    275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asp Glu Ser Leu Glu Arg Gln Met Arg Glu Met Glu Glu Asn Phe Ala
            340                 345                 350

Val Glu Ala Ala Asp Tyr Gln Asp Thr Ile Gly Arg Leu Gln Asp Glu
    355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Glu Asp Ser Leu Pro
            420                 425                 430
```

```
Leu Val Asp Thr His Ser Lys Arg Thr Leu Leu Ile Lys Thr Val Glu
        435                 440                 445

Thr Arg Asp Gly Gln Val Ile Asn Glu Thr Ser Glu His His Asp Asp
    450                 455                 460

<210> SEQ ID NO 2
<211> LENGTH: 27
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(27)
<223> OTHER INFORMATION: primer

<400> SEQUENCE: 2
gaacatatgt ccaccaggtc cgtgtcc                                           27

<210> SEQ ID NO 3
<211> LENGTH: 26
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(26)
<223> OTHER INFORMATION: primer

<400> SEQUENCE: 3
gcgacttgcc ttggcccttg agctcc                                            26

<210> SEQ ID NO 4
<211> LENGTH: 26
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(26)
<223> OTHER INFORMATION: primer

<400> SEQUENCE: 4
ccgaattcat gtccaggtcc gtgtcc                                            26

<210> SEQ ID NO 5
<211> LENGTH: 26
<212> TYPE: DNA
<213> ORGANISM: Artificial sequence
<220> FEATURE:
<223> OTHER INFORMATION: chemically synthesized
<220> FEATURE:
<221> NAME/KEY: misc_feature
<222> LOCATION: (1)..(26)
<223> OTHER INFORMATION: primer

<400> SEQUENCE: 5
ggccgcggtt caaggtcatc gtgatg                                            26

<210> SEQ ID NO 6
<211> LENGTH: 26
<212> TYPE: DNA
<213> ORGANISM: artificial sequence
<220> FEATURE:
<223> OTHER INFORMATION: chemically synthezised
<220> FEATURE:
<221> NAME/KEY: misc_feature
<222> LOCATION: (1)..(26)
<223> OTHER INFORMATION: primer
```

```
<400> SEQUENCE: 6
ccgaattcat gtccaggtcc gtgtcc                                          26

<210> SEQ ID NO 7
<211> LENGTH: 29
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(29)
<223> OTHER INFORMATION: primer

<400> SEQUENCE: 7
gtgcggccgc ccagctcctg gatttcctc                                       29

<210> SEQ ID NO 8
<211> LENGTH: 28
<212> TYPE: DNA
<213> ORGANISM: artificial sequence
<220> FEATURE:
<223> OTHER INFORMATION: chemcially synthesized
<220> FEATURE:
<221> NAME/KEY: misc_feature
<222> LOCATION: (1)..(28)
<223> OTHER INFORMATION: primer

<400> SEQUENCE: 8
cagaattcat gaacacccgc accaagag                                        28

<210> SEQ ID NO 9
<211> LENGTH: 29
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(29)
<223> OTHER INFORMATION: primer

<400> SEQUENCE: 9
cagcggccgc cttcaaggtc atcgtgatg                                       29

<210> SEQ ID NO 10
<211> LENGTH: 23
<212> TYPE: DNA
<213> ORGANISM: artificial sequence
<220> FEATURE:
<223> OTHER INFORMATION: chemcially synthesized
<220> FEATURE:
<221> NAME/KEY: misc_feature
<222> LOCATION: (1)..(23)
<223> OTHER INFORMATION: primer

<400> SEQUENCE: 10
gagtggaatt cgaggagagc agg                                             23

<210> SEQ ID NO 11
<211> LENGTH: 30
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(30)
<223> OTHER INFORMATION: primer
```

<400> SEQUENCE: 11
gccgtcgaca ttgctgcact gagtgtgtgc                                              30

<210> SEQ ID NO 12
<211> LENGTH: 97
<212> TYPE: PRT
<213> ORGANISM: Homo sapiens

<400> SEQUENCE: 12

Met Ser Thr Arg Ser Val Ser Ser Ser Tyr Arg Arg Asn Phe Gly
1               5                   10                  15

Gly Pro Gly Thr Ala Ser Arg Pro Ser Ser Ala Ser Tyr Val Thr
                20                  25                  30

Thr Ser Thr Arg Thr Tyr Ser Leu Gly Ser Ala Leu Arg Pro Ser Thr
                35                  40                  45

Ser Arg Ser Leu Tyr Ala Ser Ser Pro Gly Gly Val Tyr Ala Thr Arg
        50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys

<210> SEQ ID NO 13
<211> LENGTH: 112
<212> TYPE: PRT
<213> ORGANISM: Homo sapiens

<400> SEQUENCE: 13

Gln Ile Asp Leu Asn Met Thr Cys Arg Phe Ala Gly Val Phe His Val
1               5                   10                  15

Glu Lys Asn Gly Ala Tyr Ser Ile Ser Arg Thr Glu Ala Ala Asp Leu
                20                  25                  30

Cys Lys Ala Phe Asn Ser Thr Leu Pro Thr Met Ala Gln Met Glu Lys
            35                  40                  45

Ala Leu Ser Ile Gly Phe Glu Thr Cys Ser Ser Gly Phe Ile Glu Gly
        50                  55                  60

His Val Val Ile Pro Arg Ile His Pro Asn Ser Ile Cys Ala Ala Asn
65                  70                  75                  80

Asn Thr Gly Val Tyr Ile Leu Thr Ser Asn Thr Ser Gln Tyr Asp Thr
                85                  90                  95

Tyr Cys Phe Asn Ala Ser Ala Pro Pro Glu Glu Asp Cys Thr Ser Val
            100                 105                 110

<210> SEQ ID NO 14
<211> LENGTH: 465
<212> TYPE: PRT
<213> ORGANISM: Mesocricetus auratus

<400> SEQUENCE: 14

Met Ser Thr Arg Ser Val Ser Ser Ser Tyr Arg Arg Met Phe Gly
1               5                   10                  15

Gly Pro Gly Thr Ser Asn Arg Gln Ser Ser Asn Arg Ser Tyr Val Thr
                20                  25                  30

Thr Ser Thr Arg Thr Tyr Ser Leu Gly Ser Leu Arg Pro Ser Thr Ser
            35                  40                  45

Arg Ser Leu Tyr Ser Ser Ser Pro Gly Gly Ala Tyr Val Thr Arg Ser
        50                  55                  60

```
Ser Ala Val Arg Leu Arg Ser Ser Met Pro Gly Val Arg Leu Leu Gln
 65                  70                  75                  80

Asp Ser Val Asp Phe Ser Leu Ala Asp Ala Ile Asn Thr Glu Phe Lys
                 85                  90                  95

Asn Thr Arg Thr Asn Glu Lys Val Glu Leu Gln Glu Leu Asn Asp Arg
            100                 105                 110

Phe Ala Asn Tyr Ile Asp Lys Val Arg Phe Leu Glu Gln Gln Asn Lys
            115                 120                 125

Ile Leu Leu Ala Glu Leu Glu Gln Leu Lys Gly Gln Gly Lys Ser Arg
130                 135                 140

Leu Gly Asp Leu Tyr Glu Glu Glu Met Arg Glu Leu Arg Arg Gln Val
145                 150                 155                 160

Asp Gln Leu Thr Asn Asp Lys Ala Arg Val Glu Val Glu Arg Asp Asn
                165                 170                 175

Leu Ala Glu Asp Ile Met Arg Leu Arg Glu Lys Leu Gln Glu Glu Met
            180                 185                 190

Leu Gln Arg Glu Glu Ala Glu Ser Thr Leu Gln Ser Phe Arg Gln Asp
            195                 200                 205

Val Asp Asn Ala Ser Leu Ala Arg Leu Asp Leu Glu Arg Lys Val Glu
210                 215                 220

Ser Leu Gln Glu Glu Ile Ala Phe Leu Lys Lys Leu His Asp Glu Glu
225                 230                 235                 240

Ile Gln Glu Leu Gln Ala Gln Ile Gln Glu Gln His Val Gln Ile Asp
                245                 250                 255

Val Asp Val Ser Lys Pro Asp Leu Thr Ala Ala Leu Arg Asp Val Arg
            260                 265                 270

Gln Gln Tyr Glu Ser Val Ala Ala Lys Asn Leu Gln Glu Ala Glu Glu
            275                 280                 285

Trp Tyr Lys Ser Lys Phe Ala Asp Leu Ser Glu Ala Ala Asn Arg Asn
290                 295                 300

Asn Asp Ala Leu Arg Gln Ala Lys Gln Glu Ser Asn Glu Tyr Arg Arg
305                 310                 315                 320

Gln Val Gln Ser Leu Thr Cys Glu Val Asp Ala Leu Lys Gly Thr Asn
                325                 330                 335

Glu Ser Leu Glu Arg Gln Met Arg Glu Met Glu Glu Asn Phe Ala Leu
            340                 345                 350

Glu Ala Ala Asn Tyr Gln Asp Thr Ile Gly Arg Leu Gln Asp Glu Ile
            355                 360                 365

Gln Asn Met Lys Glu Glu Met Ala Arg His Leu Arg Glu Tyr Gln Asp
            370                 375                 380

Leu Leu Asn Val Lys Met Ala Leu Asp Ile Glu Ile Ala Thr Tyr Arg
385                 390                 395                 400

Lys Leu Leu Glu Gly Glu Glu Ser Arg Ile Ser Leu Pro Leu Pro Asn
                405                 410                 415

Phe Ser Ser Leu Asn Leu Arg Glu Thr Asn Leu Glu Ser Leu Pro Leu
            420                 425                 430

Val Asp Thr His Ser Lys Arg Thr Leu Leu Ile Lys Thr Val Glu Thr
            435                 440                 445

Arg Asp Gly Gln Val Ile Asn Glu Thr Ser Gln His His Asp Asp Leu
            450                 455                 460

Glu
465
```